(12) United States Patent
Omidbakhsh

(10) Patent No.: US 8,808,755 B2
(45) Date of Patent: Aug. 19, 2014

(54) HYDROGEN PEROXIDE-BASED SKIN DISINFECTANT

(75) Inventor: Navid Omidbakhsh, Ontario (CA)

(73) Assignee: Virox Technologies Inc., Oakville, Ontario (CA)

( * ) Notice: Subject to any disclaimer, the term of this patent is extended or adjusted under 35 U.S.C. 154(b) by 65 days.

(21) Appl. No.: 13/022,683

(22) Filed: Feb. 8, 2011

(65) Prior Publication Data

US 2011/0129435 A1    Jun. 2, 2011

Related U.S. Application Data

(63) Continuation of application No. 11/128,223, filed on May 13, 2005, now abandoned.

(60) Provisional application No. 60/570,807, filed on May 14, 2004.

(51) Int. Cl.

| | |
|---|---|
| *A01N 59/00* | (2006.01) |
| *A01N 31/04* | (2006.01) |
| *A01N 25/22* | (2006.01) |
| *A01N 41/04* | (2006.01) |
| *A61K 33/40* | (2006.01) |
| *A61K 31/31* | (2006.01) |
| *A61K 31/34* | (2006.01) |
| *A61K 31/60* | (2006.01) |

(52) U.S. Cl.
USPC ........... 424/616; 424/405; 514/159; 514/162; 514/461; 514/557; 514/558; 514/559; 514/560; 514/572; 514/574; 514/576; 514/578; 514/709; 514/711; 514/730; 514/970

(58) Field of Classification Search
USPC .......... 424/405, 616; 514/159, 162, 461, 557, 514/572, 574, 576, 578, 709, 711, 730, 970
See application file for complete search history.

(56) References Cited

U.S. PATENT DOCUMENTS

| | | | |
|---|---|---|---|
| 2,528,378 A | 10/1950 | Mannheimer | |
| 4,446,153 A | 5/1984 | Yang | |
| 5,387,605 A | 2/1995 | Beilfuss et al. | |
| 5,736,582 A | 4/1998 | Devillez | |
| 6,096,348 A | 8/2000 | Miner et al. | |
| 6,444,636 B1 | 9/2002 | Toussaint et al. | |
| 6,479,454 B1 | 11/2002 | Smith et al. | |
| 6,555,509 B2 * | 4/2003 | Abbas et al. ................. 510/143 |
| 6,617,294 B2 | 9/2003 | Narula et al. | |
| 6,627,589 B1 | 9/2003 | Arvanitidou | |
| 6,803,057 B2 | 10/2004 | Ramirez et al. | |
| 6,841,090 B1 | 1/2005 | Allighieri et al. | |
| 2002/0168422 A1 | 11/2002 | Hei et al. | |
| 2005/0019421 A1 | 1/2005 | Hobbs et al. | |

FOREIGN PATENT DOCUMENTS

| | | |
|---|---|---|
| CA | 1 102 502 | 6/1981 |
| CA | 1 244 759 | 11/1988 |
| DE | 32 29 097 A1 | 2/1984 |
| DE | 26 29 081 A1 | 6/1987 |
| DE | 35 43 500 A1 | 6/1987 |
| EP | 0 252 278 | 6/1987 |
| EP | 0351772 | 7/1989 |
| EP | 0 456 272 A1 | 5/1991 |
| EP | 0 505 935 A1 | 9/1992 |
| EP | 0 582 359 A1 | 2/1994 |
| EP | 0 582 360 A1 | 2/1994 |
| EP | 0 776 613 A1 | 6/1997 |
| EP | 1 369 037 A1 | 12/2003 |
| EP | 1 374 679 A2 | 1/2004 |
| GB | 1 584 170 | 2/1981 |
| WO | 98/18894 | 7/1988 |
| WO | 95/04001 | 2/1995 |
| WO | 97/28691 A1 | 8/1997 |
| WO | 98/18894 | 5/1998 |
| WO | 99/03446 | 1/1999 |
| WO | 99/52360 | 10/1999 |
| WO | 00/27981 | 5/2000 |
| WO | 02/055647 A1 | 7/2002 |
| WO | 03/067989 A1 | 8/2003 |
| WO | 03/076560 A1 | 9/2003 |
| WO | 2004-035718 A2 | 4/2004 |

OTHER PUBLICATIONS

Database WPI, Section Ch, Week 199615, Derwent Publications Ltd., London, GB, AN 1996-149587 XP002287351 & RU 2040275C1 (Biol Instr Mfr Res Inst) Jul. 27, 1995 abstract.
SS. Block: "Disinfection, Sterilization and Preservation", 1991, Lea & Febiger, Philadelphia, US, XP002287349, Chapter 14: G.R. Dychdala et al. "Surface-Active Agents: Acidic Anionic Compounds", pp. 256-262.
Database Chemabs 'Online!, Chemical Abstract Service, Columbus, OH, US, XP002287350 retrieved from STN-International Database accession No. 136:351642 abstract; Jul. 2, 2004.
Database WPI, Section Ch, Week 199918, Derwent Publications Ltd., London, GB, AN 1999-205420 XP002287352 & CN 1 201 594 A (Wang L), Dec. 16, 1998 abstract.
S. Block, Disinfection, Sterilization, and Preservation, Fourth Edition 1991, pags. 167-172, 178-180, 263-271, 1010-1013, 1029.

* cited by examiner

*Primary Examiner* — John Pak
*Assistant Examiner* — Nathan W Schlientz
(74) *Attorney, Agent, or Firm* — Clark & Brody

(57) ABSTRACT

A skin disinfectant in ready-to-use concentrated liquid or dry powdered form. Ready-to-use liquid forms have a pH of from about 2 to about 6 and include:
(a) hydrogen peroxide in a concentration of from about 0.01 to about 4% w/w of the solution;
(b) at least one surfactant chosen from imidazoline derivatives, alkyl betaines, alkyl amidopropyl betaine amides, alkyl amidopropyl betaines, alkylsulfo betaines, amine oxides and derivatives thereof in a concentration of from about 0.01 to about 15% w/w of the solution;
(c) at least one hydrogen peroxide stabilizer in a concentration of from about 0.01 to about 4% w/w of the solution;
(d) at least one member chosen from cyclic carboxylic acids and salts thereof in a concentration of from about 0.01 to about 4% w/w of the solution; and
(e) at least one skin conditioning agent in a concentration of from about 0.01 to about 10% w/w of the solution.

25 Claims, No Drawings

HYDROGEN PEROXIDE-BASED SKIN DISINFECTANT

This application is a continuation of U.S. application Ser. No. 11/128,223, filed 13 May 2005, now abandoned, which claims the benefit of U.S. provisional application no. 60/570,807, filed May 14, 2004 under 35 U.S.C. 119 (e).

FIELD OF THE INVENTION

The present invention relates to disinfecting solutions or formulations for use on skin containing hydrogen peroxide.

BACKGROUND OF THE INVENTION

Infection control is a major concern for health care professionals. Viruses and bacteria on contaminated hands are easily spread among people in health care facilities such as hospitals. Of course, the risk of infection is also present in public places other than hospitals, such as in gyms, washrooms, restaurants, and schools.

Washing hands with detergents or soaps is a way to reduce the risk of infection. However, in certain environments, such as hospitals, the level of disinfection required cannot be achieved by most common products. Consequently, hand disinfectants have been developed to achieve higher levels of disinfection where the need exists. These types of products generally contain alcohols, iodines/iodophors, chlorhexidine gluconate (CHG), phenolic compounds, quaternary ammonium compounds or combinations thereof.

A problem with existing products is that they often sacrifice disinfectant activity for the sake of skin mildness or vice versa. For example, while raising the concentration of the active ingredient may lead to a higher level of disinfection, such higher concentration frequently leads to increased skin irritation.

As well, many common disinfecting ingredients have inherent disadvantages. For example, while alcohols are effective in providing rapid rates of disinfection, they are flammable and therefore give rise to safety risks in use and storage. As defatting agents, they can cause dry, chapped or cracked skin on repeated use. Furthermore, their anti-microbial activity is dependent on concentration and tends to drop dramatically when used on wet hands resulting in insufficient germ kill. To overcome some of these disadvantages, it is known to include additional ingredients such as emollients, humectants, and surfactants. For example, U.S. Pat. No. 6,617,294 to Narula et al. issued Sep. 9, 2003 discloses a waterless disinfecting hand cleanser made of a combination of 60 to 90% w/w of an alcohol, silicone based materials, and humectants.

Parachlorometaxylenol (PCMX) and triclosan are common phenolic compounds used in antiseptic hand wash solutions. See, for example, European patent 505,935 B1, assigned to Becton, Dickinson and Company and granted on Feb. 4, 1998, which discloses an anti-microbial skin formulation containing PCMX, a block copolymer, and a lauryl sulfosuccinate. Although PCMX and triclosan have lower toxicity than other phenols, and are rather mild to the skin, their germicidal activity is low and depends on the formulation ingredients.

Iodine and iodophors have been used in antiseptic hand wash formulations for a long time. Their germicidal activities are low and reduced in the presence of organic matter. Furthermore, these ingredients are toxic and can irritate and stain skin.

Chlorhexidine gluconate (CHG) is used as a skin cleanser, pre-surgical scrub, germicidal hand rinse, and wound cleaner. It is less effective against gram-negative bacteria as compared to gram-positive bacteria and exhibits relatively low germicidal activity.

Hydrogen peroxide is a broad-spectrum germicide effective against bacteria, yeast, fungi, viruses and spores. It is non-toxic and its breakdown products, oxygen and water, are innocuous thus making it safe to the environment. At low concentrations (e.g. 3% w/w), it is non-irritating to skin, but exhibits low germicidal activity. For example, a solution containing 3% w/w hydrogen peroxide takes 20 minutes to achieve a greater than 6 log reduction in *Staphylococcus aureus*, which is too long for many applications. Increasing the concentration of hydrogen peroxide will increase the rate of disinfection. For example, a 25% w/w aqueous solution of hydrogen peroxide requires only 20 seconds to achieve a greater than 6 log reduction in *Staphylococcus aureus*. However, the solution is corrosive at this concentration and requires special handling procedures.

While skin disinfecting formulations exist, there is still a need for new formulations that are both safe and capable of achieving an effective rate of disinfection at realistic contact times. The present invention is intended to meet this need.

SUMMARY OF THE INVENTION

The invention provides, in accordance with a first aspect, an aqueous skin disinfecting solution having a pH of from about 2 to about 6, about 2.5 to about 5, or about 3 to about 5, and comprising:

(a) hydrogen peroxide in a concentration of from about 0.01 to about 4% w/w, from about 0.25 to about 3% w/w, or from about 1 to about 3% w/w, of the solution;

(b) at least one surfactant chosen from imidazoline derivatives, alkyl betaines, alkyl amidopropyl betaines, alkyl amidopropyl betaine amides, alkylsulfobetaines, amine oxides, and derivatives thereof, in a concentration of from about 0.01 to about 15% w/w, from about 0.3 to about 10% w/w, or from about 1 to 5% w/w, of the solution;

(c) at least one hydrogen peroxide stabilizer in a concentration of from about 0.01 to about 4% w/w, from about 0.01 to about 3% w/w, from about 0.01 to about 2% w/w, or from about 0.1 to 0.5% w/w, of the solution;

(d) at least one member chosen from cyclic carboxylic acids and salts thereof in a concentration of from about 0.01 to about 4% w/w, or from about 0.05 to about 1% w/w, of the solution;

(e) at least one skin conditioning agent in a concentration of from about 0.01 to about 10% w/w, or from about 0.5 to about 4% w/w, of the solution.

Preferred imidazoline derivatives are alkylamphocarboxylates and alkyliminocarboxylates.

The hydrogen peroxide stabilizer can be chosen from phosphoric acid, phosphonic acids having 1 to 5 phosphonic acid groups, e.g. 1-hydroxyethylidene-1,1,-diphosphonic acid, amino tri(methylene phosphonic acid), diethylenetriaminepenta(methylene phosphonic acid), 2-hydroxy ethylimino bis (methylene phosphonic acid), and ethylene diamine tetra(methylene phosphonic acid). They can also be chosen from sodium tripolyphosphate, ethylenediaminetetraacetic acid (EDTA), diethylenetriaminepentaacetic acid (DTPA), N-(hydroxyethyl)-ethylenediaminetriacetic acid (HEDTA), nitrilotriacetic acid (NTA), 2-hydroxyethyliminodiacetic acid (HEIDA), benzoic acid, aminobenzoic acid, citric acid, iminodisuccinic acid, polyaspartic acid, and salts thereof.

The cyclic carboxylic acid can be chosen from furan carboxylic acid (e.g. 2-furan carboxylic acid), benzoic acid and salicylic acid.

The skin-conditioning agent can be chosen from glycerides, sorbitol, castor oil, allantoin, cationic polymers, lanolin and its derivatives and cetyl alcohol.

The solution can further comprise at least one buffer, in a concentration of from about 0.01 to about 5% w/w of the solution, chosen from citric acid, lactic acid, glycolic acid, phosphoric acid, malic acid, succinic acid and tartaric acid.

In other embodiments, the solution can comprise at least one optional hydrogen peroxide compatible surfactant in a concentration of from about 0.01 to about 10% w/w of the solution. Exemplary hydrogen peroxide compatible surfactants are alkyl sulfate, alkyl ether sulfates, alkyl benzene sulfonic acids, alkyl sulfonic acids, alkyl diphenyl oxide sulfonic acids, naphthalene sulfonic acids, alkyl or alkenyl esters or diesters of sulfosuccinic acids, and salts thereof, alcohol ethoxylates, alkyl phenol ethoxylates, fatty acid esters, and alkylpolyglucosides.

As well, the solution can comprise at least one C1 to C8 alcohol in a concentration of from about 0.01 to about 10% w/w of solution, which may be chosen from benzyl alcohol, ethanol, n-butanol, isopropanol and glycols.

The solution can further comprise at least one member chosen from monocarboxylic acids, polycarboxylic acids, and mixtures thereof in a concentration of from about 0.01 to about 3% w/w of the solution. These ingredients have known pH buffering, stabilizing and cleaning properties. Preferred monocarboxylic acids are glycolic acid and acetic acid. A preferred polycarboxylic acid is citric acid.

To improve the rheological properties and attractiveness of the solution, the solution can further comprise at least one thickening agent compatible with hydrogen peroxide (e.g. polyacrylic acid polymers, polysaccharides, and cellulose-based polymers in a concentration of from about 0.01 to about 5% w/w of the solution, and at least one member chosen from dyes and fragrances (as are known in the art) in a concentration of from about 0.001 to about 0.5% w/w of the solution.

The balance of the solution consists of deionized water, preferably with a conductivity of less than 20 micro zimens. It will be appreciated that the lower the deionized water conductivity, the longer the shelf life.

In accordance with a second aspect of the invention, the solution may be in concentrated liquid form for dilution by the end user. Similarly, in accordance with a third aspect, the invention may take the form of a dry powdered formulation, which can be dissolved in water to form a solution according to the first aspect.

DETAILED DESCRIPTION OF THE PREFERRED EMBODIMENTS

When used herein, the expression "consisting essentially of" shall mean—including the listed ingredients and such additional ingredients as would not materially affect the basic and novel properties of the invention—. The basic and novel properties are the disinfecting properties of the invention and the suitability of the invention for use on skin.

The term "comprising" shall mean—including but not limited to—.

A "skin-conditioning agent" is any ingredient or compound, which is used to make the solution suitable for use on skin and includes moisturizers, emollients and humectants.

Certain ingredients used in the present inventive solution can serve more than one function. For example, phosphoric acid and citric acid are both hydrogen peroxide stabilizers and buffers. Similarly, benzoic acid is also a hydrogen peroxide stabilizer and a cyclic carboxylic acid, which contributes to disinfecting activity.

The inventive solution is able to provide adequate levels of disinfection while not irritating skin. The solution is non-irritating due to the low levels of hydrogen peroxide, mild surfactant package and low concentrations of other mild additives employed. The solution has broad-spectrum activity, the degree of which is unexpected given the germicidal activity of the individual ingredients. A synergy exists amongst the ingredients of the present inventive solution such that an effective disinfectant is provided that is suitable for use on skin.

Commercial solutions having hydrogen peroxide concentrations of from about 10 to about 50% w/w, (e.g. about 35% w/w or about 50% w/w), may be used to prepare solutions according to the invention. Such commercial solutions typically contain additional stabilizers and additives as are known in the art and are available from manufacturers such as FMC and Degussa AG.

As mentioned above, the invention may be in the form of a concentrated liquid for dilution by the end user. Alternatively, it may be in the form of a dry formulation for dissolution in water. In such dry formulation, the hydrogen peroxide may be supplied by persalt compounds, of which sodium percarbonate and sodium perborate in its monohydrate and tetrahydrate forms are preferred. Since sodium percarbonate contains about 20% hydrogen peroxide by weight, and sodium perborate monohydrate and sodium perborate tetrahydrate contain about 30% and about 20% respectively by weight, proper allowance must be made when blending the dry mixture of components to achieve the desired levels of hydrogen peroxide upon dissolution in water.

As noted above, certain surfactants are essential to the present invention, including, imidazoline derivatives (e.g. alkylamphoacetates, alkylamphopropionates, and alkyliminopropionates), alkylbetaines, alkylamidopropylbetaines, alkyl amidopropyl betaine amides, alkylsulfobetaines, amine oxides and derivatives and mixtures thereof. These surfactants are available from a variety of sources, including Rhodia, which manufactures and sells imidazoline derivatives in association with the trademark MIRANOL and an alkylamidopropylbetaine in association with the trademark MIRATAIN E. Seppic manufactures and sells surfactants useful in the present invention in association with the trademark MONTALINE. Cognis manufactures and sells useful surfactants in association with the trademark DEHYTON. Stepan manufactures and sells amine oxides in association with the trademark AMMONYX. Lonza manufactures and sells imidazoline derivative and alky betaines in association with the trademarks AMPHOTERGE and LONZAINE.

Amine oxides useful in this invention are $R_1R_2R_3NO$ wherein each of $R_1$, $R_2$, and $R_3$ is independently a saturated, substituted or unsubstituted linear or branched alkyl group having from 1 to 28 carbon atoms.

Preferred imidazoline derivatives are alkylamphocarboxylates and alkyliminocarboxylates having the following structures:

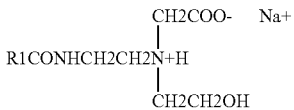

-continued

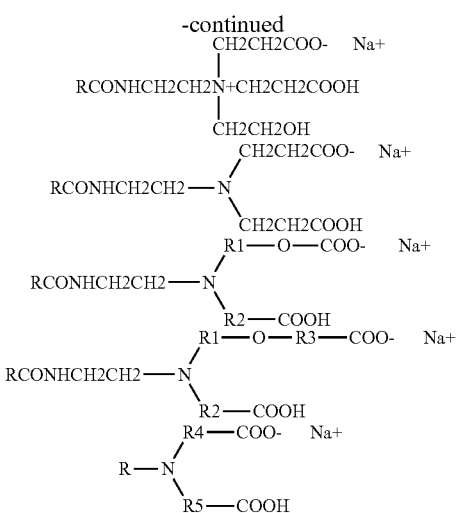

wherein R is a saturated, substituted or unsubstituted linear or branched alkyl group having from 1 to 24 carbon atoms. Preferably, R is a linear alkyl chain having from 8 to 16 carbon atoms and R1 to R5 are saturated, linear alkyl groups having from 1 to 3 carbon atoms.

Alkyl amidopropyl betaine amides useful in this invention have a saturated, substituted or unsubstituted linear or branched alkyl group having from 1 to 24 carbon atoms. The alkyl group is preferably a linear chain having from 6 to 16 carbon atoms.

Alkyl amidosulfobetaines have the following structure:

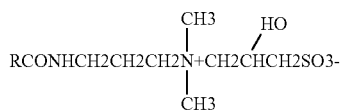

wherein R is a saturated, substituted or unsubstituted linear or branched alkyl group having from 1 to 24 carbon atoms. The alkyl group is preferably a linear alkyl chain having 8 to 16 carbon atoms.

Preferred hydrogen peroxide stabilizers are available from a number of manufacturers including Rhodia under the trademark BRIQUEST, and Solutia under the trademark DEQUEST.

The invention will be better understood with reference to the following examples. In such examples, the following ingredients were used.

Hydrogen Peroxide
  The hydrogen peroxide used in all the examples is a 50% w/w technical grade commercial solution sold by Degussa AG.

Hydrogen Peroxide Stabilizer
  BRIQUEST ADPA 60 AW: 1-hydroxyethylidene-1,1,-diphosphonic acid, sold by Rhodia as a 60% w/w solution.
  BRIQUEST 301-50A: nitrilotris (methylenephosphonic acid), sold by Rhodia as a 50% w/w solution.
  VERSENE 100: tetrasodium ethylenediaminetetraacetate, sold by Dow Chemicals as a 37% w/w solution.
  VERSENE NTA 148: trisodium nitrilotriacetate, sold by Dow Chemicals as a 38% w/w solution.
  VERSENE HEIDA: disodium salt of 2-hydroxyethyliminodiacetic acid, sold by Dow Chemicals as a 41% w/w solution.
  BAYPURE CX: Sodium salt of iminodisuccinic acid, sold by Lanxess as a 100% w/w powder.
  BAYPURE DS: Sodium salt of polyaspartic acid, sold by Lanxess as a 100% w/w powder.

Surfactants
  DEHYTON MC: sodium cocoamphoacetate, sold by Cognis as a 40% w/w solution.
  AMPHOTERGE K-2: disodium cocamphopropionate, sold by Lonza as a 40% w/w solution.
  AMPHOSOL CG: cocamidopropyl betaine, sold by Stepan as a 30% w/w solution.
  MIRANOL C2M CONC NP: cocampho diacetate, sold by Rhodia as a 30% w/w solution.
  MONTALINE C40: cocamidopropyl betaineamide monoethanolamine chloride (quaternized coconut oil), sold by Seppic as a 38% w/w solution.
  LONZAINE 16SP: cetyl dimethyl betaine, sold by Lonza as a 35% w/w solution.
  MIRATAINE CBS: Cocamido propyl hydroxy sultaine, sold by Rhodia as a 43.5% w/w solution.
  AMMONYX LO: lauramine oxide, sold by Stepan as a 30% w/w solution.
  AMMONYX CDO: cocamidopropylamine oxide, sold by Stepan as a 30% w/w solution.

Skin Conditioning Agents
  POLYQUATERNIUM-11: cationic copolymer of vinylpyrrolidone and dimethylaminoethylmethacrylate quaternized with diethyl sulfate, sold by ISP as a 20% w/w solution.
  POLYQUATERNIUM-7: cationic copolymer of dimethyldiallylammonium chloride and acrylamide, sold by McIntyre Group Ltd. as a 9% w/w solution.
  MERGITAL EL33: polyethylene glycol castor oil, sold by Cognis as a 9% w/w solution.
  Glycerin Additional Optional Surfactants
  STEPAN MILD SL3 BA: disodium lauryl ether sulfosuccinate ethoxylated to 3 moles ethylene oxide (EO), sold by Stepan as a 32% w/w solution.
  SURFYNOL 104PG-50: 2,4,7,9 tetramethyl-5 decyne-4,7 diol, sold by Air Products as a 50% w/w solution.
  ETHAL OA-23: Oleyl (C18) alcohol ethoxylate, 23 moles of EO/mole of alcohol, sold by Ethox Company as a 70% w/w solution.
  TERGITOL 15-S-7: C11-C14 secondary alcohol ethoxylate, 7 moles of EO/mole of alcohol, sold by Union Carbide as a 100% w/w liquid.
  TERGITOL 15-S-5: C11-C14 secondary alcohol ethoxylate, 5 moles of EO/mole of alcohol, sold by Union Carbide as a 100% w/w liquid.

Thickening Agents
  CARBOPOL 676: acrylic polymer, sold by Noveon Company as a 100% w/w powder.
  NATRASOL 250 HR: Hydroxyethylcellulose, sold by Hercules as a 100% w/w powder.
  KLUCELL HF: Hydroxypropylcellulose, sold by Hercules as a 100% w/w powder.

EXAMPLES

| SOLUTION 1 | | |
|---|---|---|
| INGREDIENTS | % w/w | Actual concentration % w/w |
| deionized water | Up to 100 | Up to 100 |
| BRIQUEST ADPA 60 AW | 0.6 | 0.36 |
| salicylic acid | 0.01 | 0.01 |
| Glycerin | 3 | 3 |
| DEHYTON MC | 3 | 1.2 |
| MONTALINE C40 | 1 | 0.38 |
| AMMONYX CDO | 3 | 0.9 |
| benzoic acid | 0.2 | 0.2 |
| POLYQUATERNIUM-11 | 0.8 | 0.16 |
| MERGITAL EL33 | 1 | 0.09 |
| hydrogen peroxide | 4 | 2 |
| pH | | 4 |

Solution 1 is a hand disinfectant, which, at a 55% dilution achieved a greater than 4 log 10 reduction in *Staphylococcus aureus* and *E. coli* at 30 second contact time using European suspension test method EN.12054. The solution was also tested against these organisms in vivo using European finger-pad test method EN.1499.

Test method EN.1499 involves preparing 2 liters of a contamination fluid containing from $2 \times 10^8$-$2 \times 10^9$ test organisms. The test organisms are prepared in Tryptone Soy Broth TSB and pooled overnight. Hands are washed with soft soap and water to remove any soil and then dried. The hands are then immersed up to the mid-metacarpals in the contamination fluid with the fingers spread apart. Immersion is for 5 seconds. The hands are then air dried for 3 minutes while moving the hands to avoid droplet formation.

Immediately after drying, the hands are sampled to establish a baseline or "pre-value" count of test organisms. This is achieved by rubbing the fingertips (including the thumb) against the base of a petri dish containing 10 ml TSB on a neutralization bath (designed to neutralize the activity of the test product) for 60 seconds. A separate petri dish is used for each hand. A series of 10-fold dilutions of the neutralization bath is prepared and each dilution is plated on a well-dried Tryptone Soy Agar (TSA) plate and incubated at 37° C. for 18-24 hours. The number of surviving colony forming units of microorganisms on each plate is then counted and the value is expressed in terms of log 10.

The product to be tested is poured into cupped hands which had been dipped in the contaminated fluid in the same manner described above. The product is rubbed vigorously into the skin up to the wrists for 60 seconds to ensure total coverage of the hands. The fingers are then rinsed under running tap water for 15 seconds and excess water is shaken off.

The hands are then sampled individually to establish a post treatment or "post-value" count of test organisms. This is performed using exactly the same method as that used to establish the pre-value count. That is, the fingertips (including the thumb) are rubbed against the base of a petri dish (one for each hand) containing 10 ml TSB in a neutralization bath for 60 seconds. A series of 10-fold dilutions of the neutralization bath is prepared and each dilution is plated on a well-dried TSA plate and incubated at 37° C. for 18-24 hours. The number of surviving colony forming units of microorganisms on each plate is then counted and the value is expressed in terms of log 10.

5 ml of a soft soap which does not have any antimicrobial active ingredients, is used as a control and tested in the above same manner.

After recording the number of colony forming units for each dilution of the sample neutralization fluid, the number of colony forming units per ml is calculated and expressed in terms of log 10. For both test and control products, the mean log counts from left and right hands are used to determine the pre- and post-values. The difference between the mean pre-value and the mean post-value counts is then calculated and a log reduction factor for the test product and the control product is calculated using the WILCOXON's ranked pairs test. For a product to conform to standard EN.1499, the log 10 reductions calculated for the test product must be significantly better (pr=0.01) than those calculated for the control product.

Test method EN.12054 is a suspension test method, which entails pipetting 9.0 ml of the test solution into a 25 ml capacity sterile container. 1 ml of a bacterial test suspension is then added and mixed with the test solution. The container is then placed in a water bath at 20±1° C. for a defined contact time. Just before conclusion of the defined contact time, the solution is mixed and 1.0 ml is transferred into a tube containing 8 ml of a neutralizer and 1 ml of water. The solution is then mixed again and the tube is placed in a water bath at 20±1° C. After a neutralization time of 5 minutes±10 seconds, a series of ten-fold dilutions of the neutralized mixture is prepared. A sample of 1 ml of the mixture and 1 ml of its $10^{-1}$ dilution is taken in duplicate and incubated by using the pour plate or spread plate technique. In the pour plate technique, each 1 ml sample of the mixture is pipetted onto a separate petri dish containing 12 to 15 ml of melted TSA cooled to 45±1° C. In the spread plate technique, each 1 ml sample of the mixture is spread on an appropriate number of oven-dried plates containing TSA.

The plates are then incubated at 36±1° C. for 24 hours after which the number of colony forming units for each plate is determined. The plates are incubated for another 24 hours and the colony forming units are recounted. The highest count value for each plate is used to determine the effectiveness of the test solution. Results are expressed in terms of log 10. A 3-log reduction is the criteria for passing this test method.

| SOLUTION 2 | | |
|---|---|---|
| INGREDIENTS | % w/w | Actual concentration % w/w |
| deionized water | Up to 100 | Up to 100 |
| citric acid | Up to pH = 4 | Up to pH = 4 |
| Glycerin | 1 | 1 |
| BRIQUEST ADPA 60 AW | 0.6 | 0.36 |
| STEPAN MILD SL3 BA | 4 | 1.28 |
| AMMONYX LO | 0.7 | 0.21 |
| POLYQUATERNIUM-11 | 0.8 | 0.16 |
| hydrogen peroxide | 6 | 3 |

Solution 2 does not contain any cyclic carboxylic acids and is therefore not in accordance with the present invention. This solution (at 55% dilution) failed the in vitro European suspension test method EN.12054 using a contact time of 1 minute.

| SOLUTION 3 | | |
|---|---|---|
| INGREDIENTS | % w/w | Actual concentration % w/w |
| deionized water | Up to 100 | Up to 100 |
| citric acid | 0.1 | 0.1 |
| glycerin | 1 | 1 |
| BRIQUEST ADPA 60 AW | 0.6 | 0.36 |
| STEPAN MILD SL3 BA | 4 | 1.28 |
| salicylic acid | 0.17 | 0.17 |
| POLYQUATERNIUM-11 | 0.8 | 0.16 |

SOLUTION 3

| INGREDIENTS | % w/w | Actual concentration % w/w |
|---|---|---|
| hydrogen peroxide | 6 | 3 |
| KOH | Up to pH = 4.0 | Up to pH = 4.0 |

Solution 3 does not contain any surfactants which are essential to the present invention and is therefore not in accordance with the present invention. This solution (at 55% dilution) failed the in vitro European suspension test method EN.12054 using a contact time of 1 minute.

What follows are additional exemplary solutions according to the present invention.

| INGREDIENTS | SOLUTION 4 % w/w | SOLUTION 5 % w/w | SOLUTION 6 % w/w | SOLUTION 7 % w/w | SOLUTION 8 % w/w |
|---|---|---|---|---|---|
| deionized water | | | Qs to 100 | | |
| hydrogen peroxide | 3 | 4 | 3 | 3 | 3 |
|  | 1.5 | 2 | 1.5 | 1.5 | 1.5 |
| benzoic acid | 0.17 | 0.17 | 0.15 | 0.17 | 0.17 |
|  | 0.17 | 0.17 | 0.15 | 0.17 | 0.17 |
| BRIQUEST ADPA 60 AW | 0.5 | 0.5 | 0.5 | 0.5 | 0.5 |
|  | 0.3 | 0.3 | 0.3 | 0.3 | 0.3 |
| lactic acid | — | — | — | — | 0.5 |
|  | — | — | — | — | 0.4 |
| DEHYTON MC | 0.5 | 0.5 | 0.5 | 0.5 | 0.5 |
|  | 0.2 | 0.2 | 0.2 | 0.2 | 0.2 |
| AMMONYX CDO | — | 0.5 | 0.2 | 0.5 | 0.5 |
|  | — | 0.15 | 0.06 | 0.15 | 0.15 |
| MIRANOL C2M CONC NP | — | — | 0.5 | 0.7 | 0.7 |
|  | — | — | 0.15 | 0.21 | 0.21 |
| MERGITAL EL33 | 2.5 | 1.0 | — | — | — |
|  | 0.225 | 0.09 | — | — | — |
| sorbitol | — | — | 2.0 | — | — |
|  | — | — | 2.0 | — | — |
| glycerin | 3.0 | — | — | 2.5 | 4.0 |
|  | 3.0 | — | — | 2.5 | 4.0 |
| benzyl alcohol | — | — | — | — | 2.5 |
|  | — | — | — | — | 2.5 |
| isopropyl alcohol | — | — | — | 2.0 | — |
|  | — | — | — | 1.4 | — |
| NaOH (50%) | To pH = 3.0 | To pH = 5.5 | To pH = 5.0 | To pH = 5.0 | To pH = 4.0 |

| INGREDIENTS | SOLUTION 9 % w/w | SOLUTION 10 % w/w | SOLUTION 11 % w/w | SOLUTION 12 % w/w | SOLUTION 13 % w/w |
|---|---|---|---|---|---|
| deionized water | | | Qs to 100 | | |
| hydrogen peroxide | 3 | 4 | 3 | 4 | 3 |
|  | 1.5 | 2 | 1.5 | 2 | 1.5 |
| benzoic acid | — | 0.17 | — | 0.17 | 0.17 |
|  | — | 0.17 | — | 0.17 | 0.17 |
| salicylic acid | — | — | 0.15 | 0.02 | — |
|  | — | — | 0.15 | 0.02 | — |
| 2-furan carboxylic acid | 0.5 | — | — | — | — |
|  | 0.5 | — | — | — | — |
| BRIQUEST 301-50A | 0.5 | 0.5 | — | — | 0.5 |
|  | 0.25 | 0.25 | — | — | 0.25 |
| VERSENE NTA 148 | — | — | — | 0.5 | — |
|  | — | — | — | 0.5 | — |
| VERSENE 100 | — | — | 0.4 | — | — |
|  | — | — | 0.4 | — | — |
| MIRANOL C2M CONC NP | 25 | 40 | 7 | 10 | — |
|  | 7.5 | 12 | 2.1 | 3 | — |
| ETHAL OA-23 | — | 0.05 | 0.05 | 0.1 | 0.07 |
|  | — | 0.04 | 0.04 | 0.07 | 0.05 |
| AMMONYX CDO | 20 | — | 10 | 0.5 | — |
|  | 6 | — | 3 | 0.15 | — |
| NATRASOL 250 HR | — | — | 0.5 | — | — |
|  | — | — | 0.5 | — | — |
| glycerin | — | — | 5.0 | — | — |
|  | — | — | 5.0 | — | — |
| benzyl alcohol | — | — | — | — | 2.0 |
|  | — | — | — | — | 2.0 |

-continued

| INGREDIENTS | | | | | |
|---|---|---|---|---|---|
| isopropyl alcohol | — | — | — | 2.0 | — |
|  | — | — | — | 1.4 | — |
| NaOH (50%) | To pH = 2.5 | To pH = 3.5 | To pH = 5.0 | To pH = 6.0 | To pH = 5.0 |

| | SOLUTION | | | | |
|---|---|---|---|---|---|
| INGREDIENTS | 14 % w/w | 15 % w/w | 16 % w/w | 17 % w/w | 18 % w/w |
| deionized water | | | Qs to 100 | | |
| hydrogen peroxide | 3 | 4 | 3 | 4 | 3 |
|  | 1.5 | 2 | 1.5 | 2 | 1.5 |
| benzoic acid | — | 0.17 | — | 0.17 | 0.17 |
|  | — | 0.17 | — | 0.17 | 0.17 |
| salicylic acid | — | — | 0.15 | 0.02 | — |
|  | — | — | 0.15 | 0.02 | — |
| 2-furan carboxylic acid | 0.5 | — | — | — | — |
|  | 0.5 | — | — | — | — |
| BRIQUEST 301-50A | 0.5 | 0.5 | 0.5 | 0.5 | 0.5 |
|  | 0.25 | 0.25 | 0.25 | 0.25 | 0.25 |
| citric acid | — | 1.0 | — | — | — |
|  | — | 1.0 | — | — | — |
| AMPHOSOL CG | 0.3 | 0.5 | — | 0.7 | 0.7 |
|  | 0.09 | 0.15 | — | 0.21 | 0.21 |
| SURFYNOL 104PG-50 | 0.1 | 0.05 | 0.05 | 0.1 | 0.07 |
|  | 0.05 | 0.03 | 0.03 | 0.05 | 0.04 |
| AMMONYX LO | — | — | 6.0 | 0.5 | 0.5 |
|  | — | — | 1.8 | 0.15 | 0.15 |
| CARBOPOL 676 | 0.3 | — | — | — | — |
|  | 0.3 | — | — | — | — |
| sorbitol | 4.0 | — | — | — | — |
|  | 4.0 | — | — | — | — |
| benzyl alcohol | — | — | — | — | 2.0 |
|  | — | — | — | — | 2.0 |
| isopropyl alcohol | — | — | — | 2.0 | — |
|  | — | — | — | 1.4 | — |
| NaOH (50%) | To pH = 2.5 | To pH = 3.0 | To pH = 5.0 | To pH = 6.0 | To pH = 5.0 |

| | SOLUTION | | | | |
|---|---|---|---|---|---|
| INGREDIENTS | 19 % w/w | 20 % w/w | 21 % w/w | 22 % w/w | 23 % w/w |
| deionized water | | | Qs to 100 | | |
| hydrogen peroxide | 3 | 4 | 3 | 4 | 3 |
|  | 1.5 | 2 | 1.5 | 2 | 1.5 |
| benzoic acid | — | 0.2 | — | 0.15 | 0.17 |
|  | — | 0.2 | — | 0.15 | 0.17 |
| salicylic acid | — | — | 0.15 | 0.04 | — |
|  | — | — | 0.15 | 0.04 | — |
| 2-furan carboxylic acid | 0.3 | — | — | — | — |
|  | 0.3 | — | — | — | — |
| BRIQUEST 301-50A | 0.4 | 0.5 | 0.5 | 0.5 | 0.5 |
|  | 0.2 | 0.25 | 0.25 | 0.25 | 0.25 |
| citric acid | — | 1.0 | — | — | — |
|  | — | 1.0 | — | — | — |
| AMPHOTERGE K-2 | 0.7 | 0.8 | 0.8 | 1.0 | 0.5 |
|  | 0.28 | 0.32 | 0.32 | 0.4 | 0.2 |
| AMMONYX LO | — | — | 0.2 | 0.5 | 0.5 |
|  | — | — | 0.06 | 0.15 | 0.15 |
| KLUCEL HF | — | 0.5 | — | — | — |
|  | — | 0.5 | — | — | — |
| allantoin | — | 0.05 | — | — | — |
|  | — | 0.05 | — | — | — |
| glycerin | 10 | 4.0 | 5.0 | 2.0 | 3.0 |
|  | 10 | 4.0 | 5.0 | 2.0 | 3.0 |
| benzyl alcohol | — | — | — | — | 2.0 |
|  | — | — | — | — | 2.0 |
| isopropyl alcohol | — | — | — | 2.0 | — |
|  | — | — | — | 1.4 | — |
| NaOH (50%) | To pH = 2.5 | To pH = 3.5 | To pH = 5.0 | To pH = 6.0 | To pH = 5.0 |

-continued

|  | SOLUTION | | | | | |
|---|---|---|---|---|---|---|
| INGREDIENTS | 24 % w/w | 25 % w/w | 26 % w/w | 27 % w/w | 28 % w/w | 29 % w/w |
| deionized water | Qs to 100 | | | | | |
| hydrogen peroxide | 6 3 | 8 4 | 8 4 | 8 4 | 8 4 | 1.0 0.5 |
| benzoic acid | 0.2 0.2 | 0.1 0.1 | 0 0 | 0.1 0.1 | 0.1 0.1 | 0.1 0.1 |
| salicylic acid | — — | 0.1 0.1 | 0.2 0.2 | 0.1 0.1 | 0.1 0.1 | 0.1 0.1 |
| BRIQUEST ADPA 60AW | 3.0 0.18 | 4.0 2.4 | 4.0 2.4 | 4.0 2.4 | — — | 2.4 2.4 |
| VERSENA HEIDA | — — | — — | — — | — — | 4.0 1.6 | 2.5 1.0 |
| citric acid | 1.0 1.0 | 1.0 1.0 | 1.0 1.0 | 1.0 1.0 | 1.0 1.0 | 1.0 1.0 |
| TERGITOL 15-S-7 | 5.0 5.0 | 7.0 7.0 | 7.0 7.0 | 7.0 7.0 | 7.0 7.0 | 7.0 7.0 |
| TERGITOL 15-S-5 | 2.0 2.0 | 3.0 3.0 | 3.0 3.0 | 3.0 3.0 | 3.0 3.0 | 3.0 3.0 |
| ETHAL OA-23 | 0.2 0.14 | 0.1 0.07 | 3.0 2.1 | 1.2 0.84 | 1.2 0.84 | 1.2 0.84 |
| glycolic acid | 2.0 1.2 | 1.0 0.6 | 1.0 0.6 | 1.0 0.6 | 1.0 0.6 | 1.0 0.6 |
| phosphoric acid | — — | 1.0 0.75 | 1.0 0.75 | 1.0 0.75 | 1.0 0.75 | 1.0 0.75 |
| AMMONYX LO | 3.0 0.9 | 2.0 0.6 | 2.0 0.6 | 14 4.2 | 5.0 1.5 | 5.0 1.5 |
| AMPHOSOL CG | 5.0 1.5 | — — | — — | — — | 5.0 1.5 | 5.0 1.5 |
| MONTALINE C40 | 4.0 1.6 | — — | 10 4.0 | — — | 4.0 1.6 | 4.0 1.6 |
| MIRANOL C2M CONC NP | — — | — — | — — | 7.0 2.1 | 5.0 1.5 | 5.0 1.5 |
| glycerin | 3.0 3.0 | 1.0 1.0 | 2.0 2.0 | 7.0 7.0 | 8.0 8.0 | 4.0 4.0 |
| propylene glycol | 0 0 | 0 0 | 0 0 | 1.0 1.0 | 1.0 1.0 | 1.0 1.0 |
| NaOH (50%) | To pH = 4.0 | | | | | |

|  | SOLUTION | |
|---|---|---|
| INGREDIENTS | 30 % w/w | 31 % w/w |
| deionized water | Qs to 100 | |
| hydrogen peroxide | 3 1.5 | 4 2.0 |
| benzoic acid | — — | 0.2 0.2 |
| salicylic acid | 0.15 0.15 | — — |
| BRIQUEST 301-50A | 0.4 0.2 | 0.5 0.25 |
| citric acid | — — | 1.0 1.0 |
| LONZAINE 16SP | 5.0 1.8 | — — |
| MIRATAINE CBS | — — | 3.0 1.3 |
| AMMONYX LO | 1.0 0.3 | 0.3 0.1 |
| CARBOPOL 676 | — — | 0.5 0.5 |
| allantoin | — — | 0.05 0.05 |
| glycerin | — — | 4.0 4.0 |
| sorbitol | 5.0 5.0 | — — |
| NAOH (50% | Up to pH = 4 | Up to pH = 5 |
| pH | 4 | 5 |

-continued

| INGREDIENTS | SOLUTION | | | |
|---|---|---|---|---|
| | 32 % w/w | 33 % w/w | 34 % w/w | 35 % w/w |
| deionized water | Qs to 100 | | | |
| hydrogen peroxide | 6 | 8 | 6 | 8 |
| | 3 | 4 | 3 | 4 |
| benzoic acid | 0.17 | 0.1 | 0.17 | 0.1 |
| | 0.17 | 0.1 | 0.17 | 0.1 |
| salicylic acid | 0.17 | 0.1 | 0.17 | 0.1 |
| | 0.17 | 0.1 | 0.17 | 0.1 |
| BRIQUEST ADPA 60AW | 0.35 | 4.0 | — | — |
| | 0.21 | 2.4 | | |
| BAYPURE CX | — | — | — | 0.5 |
| | | | | 0.5 |
| BAYPURE DS | — | — | 0.4 | — |
| | | | 0.4 | |
| citric acid | 0.1 | 1.0 | 0.1 | 1.0 |
| | 0.1 | 1.0 | 0.1 | 1.0 |
| AMMONYX LO | 3.0 | 2.0 | 3.0 | 2.0 |
| | 0.9 | 0.6 | 0.9 | 0.6 |
| AMPHOSOL CG | 6.0 | — | 6.0 | — |
| | 1.8 | | 1.8 | |
| MONTALINE C40 | 4.0 | — | 4.0 | — |
| | 1.6 | | 1.6 | |
| POLYQUATERNIUM-7 | 0.8 | — | 0.8 | — |
| | 0.07 | | 0.07 | |
| Glycerin | 3.0 | — | 3.0 | — |
| | 3.0 | | 3.0 | |
| NATRASOL 250 HR | — | 0.5 | — | 0.5 |
| | | 0.5 | | 0.5 |
| KOH (45%) | Up to the specified pH | | | |
| pH | 3.0 | 2.0 | 4.0 | 5.0 |

The active concentration in final solution is shown in bold.

Solution 32 was tested for its microbial activity using EN.12054 test method at 55% dilution against *S. aureus*, *P. aeruginosa*, *E. hirae*, and *E. coli* and showed more than 3 log reduction which is the criteria for a hand antiseptic. This solution was also tested against *E. coli* using EN.1499 and passed the test.

Solution 32 was also tested for its skin irritation using a patch test. In this study, the solution was put on patches and applied on the skin of 11 volunteers for 48 hours. No irritation was observed after the test, indicating that the solution is not a skin irritant.

Solution 32 was also tested for its hydrogen peroxide stability using a hot stability test method. The solution was kept at 70° C. for one week, which is equivalent to 1 year at room temperature. The loss for hydrogen peroxide was less than 5% proving remarkable stability of the solution.

The foregoing description is by way of example only and shall not be construed to limit the scope of the invention as defined by the following claims.

The invention claimed is:

1. A method of disinfecting skin comprising applying an aqueous skin disinfecting solution to skin, the solution being suitable for use on skin, having a pH of from about 2 to about 6, and consisting of:
  (a) hydrogen peroxide in a concentration of from about 0.01 to about 4% w/w of the solution;
  (b) at least one amine oxide surfactant in a concentration of from about 0.01 to about 15% w/w of the solution;
  (c) at least one hydrogen peroxide stabilizer in a concentration of from about 0.01 to about 4% w/w of the solution;
  (d) salicylic acid in a concentration of from about 0.01 to about 4% w/w of the solution;
  (e) at least one skin conditioning agent in a concentration of from about 0.01 to about 10% w/w of the solution;
  (f) optionally, at least one buffer in a concentration of from about 0.01 to about 5% w/w of the solution;
  (g) optionally, at least one thickening agent compatible with hydrogen peroxide in a concentration of from about 0.01 to about 5% w/w of the solution;
  (h) optionally, at least one additional surfactant selected from the group consisting of alkyl amphocarboxylates, alkyl betaines, alkyl amidopropyl betaine amides, alkyl amidopropyl betaines, and alkylsulfo betaines, in a concentration of from about 0.01 to about 15% w/w of the solution;
  (i) optionally, at least one C1 to C8 alcohol in a concentration of from about 0.01 to about 10% w/w of solution;
  (j) optionally, at least one member selected from the group consisting of monocarboxylic acids, polycarboxylic acids, and mixtures thereof in a concentration of from about 0.01 to about 3% w/w of the solution;
  (k) optionally, at least one member selected from the group consisting of dyes and fragrances in a concentration of from about 0.001 to about 0.5% w/w of the solution; and
  (l) water q.s. to 100% w/w.

2. The method of claim 1, wherein the pH of the solution is from about 2 to about 4.

3. The method of claim 2, wherein the solution has a pH from about 2.5 to about 3.5.

4. The method of claim 1, wherein the skin conditioning agent is selected from the group consisting of glycerin, glycerides, sorbitol, castor oil, allantoin, cationic polymers, lanolin, and cetyl alcohol.

5. The method of claim 4, wherein the skin conditioning agent is selected from the group consisting of glycerin, castor oil, and cationic polymers.

6. The method of claim 1, wherein the buffer is present.

7. The method of claim 6, wherein the buffer is selected from the group consisting of citric acid, lactic acid, glycolic acid, phosphoric acid, malic acid, succinic acid and tartaric acid.

8. The method of claim 1, wherein the hydrogen peroxide stabilizer is selected from the group consisting of phosphoric acid, phosphonic acids having 1 to 5 phosphonic acid groups, ethylenediaminetetraacetic acid (EDTA), diethylenetriaminepentaacetic acid (DTPA), N-(hydroxyethyl)-ethylenediaminetriacetic acid (HEDTA), nitrilotriacetic acid (NTA), 2-hydroxyethyliminodiacetic acid (HEIDA), benzoic acid, aminobenzoic acid, citric acid, iminodisuccinic acid, polyaspartic acid, and salts thereof.

9. The method of claim 8, wherein the hydrogen peroxide stabilizer is selected from the group consisting of sodium tripolyphosphate, 1-hydroxyethylidene-1,1,-diphosphonic acid, amino tri(methylene phosphonic acid), diethylenetriaminepenta(methylene phosphonic acid), 2-hydroxy ethylimino bis(methylene phosphonic acid), and ethylene diamine tetra(methylene phosphonic acid).

10. The method of claim 1, wherein the at least one thickening agent compatible with hydrogen peroxide is present.

11. The method of claim 10, wherein the thickening agent is selected from the group consisting of polyacrylic acid polymers, polysaccharides, and cellulose based polymers.

12. The method of claim 1, wherein the solution has a hydrogen peroxide concentration of from about 0.25 to about 3% w/w of the solution.

13. The method of claim 1, wherein the at least one additional surfactant selected from the group consisting of alkyl amphocarboxylates, alkyl betaines, alkyl amidopropyl betaine amides, alkyl amidopropyl betaines, and alkylsulfo betaines, is present.

14. The method of claim 1, wherein the at least one hydrogen peroxide stabilizer is selected from the group consisting of benzoic acid and phosphoric acid.

15. The method of claim 1, wherein the at least one additional surfactant is present in a concentration of from about 0.01 to about 10% w/w of the solution.

16. The method of claim 1, wherein the at least one C1 to C8 alcohol is selected from the group consisting of benzyl alcohol, ethanol, n-butanol, isopropanol, and glycols.

17. The method of claim 1, wherein the at least one member selected from the group consisting of monocarboxylic acids, polycarboxylic acids, and mixtures thereof is present.

18. The method of claim 1, wherein the at least one amine oxide is present in a concentration of from about 1 to about 5% w/w of the solution.

19. The method of claim 1, wherein the at least one hydrogen peroxide stabilizer is present in a concentration of from about 0.01 to about 2% w/w of the solution.

20. The method of claim 1, wherein the salicylic acid is present in a concentration of from about 0.05 to about 1% w/w of the solution.

21. The method of claim 1, wherein the at least one skin conditioning agent is present in a concentration of from about 0.5 to about 10% w/w of the solution.

22. The method of claim 1, wherein the at least one C1 to C8 alcohol is present.

23. The method of claim 1, wherein the at least one member selected from the group consisting of dyes and fragrances is present.

24. The method of claim 1, where the amine oxide has the formula, R1R2R3NO, wherein each of R1, R2, R3 is independently a saturated, substituted or unsubstituted, linear or branched alkyl group having from 1 to 28 carbon atoms.

25. The method of claim 24, wherein the amine oxide is selected from the group consisting of lauramine oxide and cocamidopropylamine oxide.

* * * * *

UNITED STATES PATENT AND TRADEMARK OFFICE
CERTIFICATE OF CORRECTION

PATENT NO. : 8,808,755 B2  
APPLICATION NO. : 13/022683  
DATED : August 19, 2014  
INVENTOR(S) : Omidbakhsh et al.

Page 1 of 1

It is certified that error appears in the above-identified patent and that said Letters Patent is hereby corrected as shown below:

On the Title Page

Add Pierre Grascha as Inventor as follows:

(75) Inventor: Navid Omidbakhsh, Ontario (CA); Pierre Grascha, Cormontreuil (FR)

Signed and Sealed this  
Twenty-third Day of June, 2015

Michelle K. Lee  
*Director of the United States Patent and Trademark Office*